(12) United States Patent
Au

(10) Patent No.: US 6,373,392 B1
(45) Date of Patent: Apr. 16, 2002

(54) ALERT DEVICE FOR PROVIDING A WARNING OF A BABY'S CONDITION WHICH MAY LEAD TO THE ONSET OF SIDS

(76) Inventor: Eric Au, 12 Webber Parade, East Keilor, Victoria 3033 (AU)

( * ) Notice: Subject to any disclaimer, the term of this patent is extended or adjusted under 35 U.S.C. 154(b) by 0 days.

(21) Appl. No.: 09/529,449
(22) PCT Filed: Oct. 15, 1998
(86) PCT No.: PCT/AU98/00850
§ 371 Date: Apr. 24, 2000
§ 102(e) Date: Apr. 24, 2000
(87) PCT Pub. No.: WO99/18843
PCT Pub. Date: Apr. 22, 1999

(30) Foreign Application Priority Data
Oct. 15, 1997 (AU) .............................................. PO9801

(51) Int. Cl.[7] ............................................. G08B 23/00
(52) U.S. Cl. .................... 340/573.1; 340/575; 340/586; 340/588; 340/589; 600/534; 600/535; 600/549
(58) Field of Search ............................. 340/573.1, 575, 340/586, 588, 589, 611, 614, 870.17; 600/534, 535, 549

(56) References Cited

U.S. PATENT DOCUMENTS

| 4,296,757 A | * | 10/1981 | Taylor | 600/534 |
| 4,747,413 A | * | 5/1988 | Bloch | 600/549 |
| 5,033,864 A | * | 7/1991 | Lasecki et al. | 600/549 |
| 5,107,855 A | * | 4/1992 | Harrington et al. | 600/534 |
| 5,615,688 A | | 4/1997 | O'Dwyer | 128/716 |
| 5,726,631 A | * | 3/1998 | Lin | 340/573 |

FOREIGN PATENT DOCUMENTS

| FR | 9509744 | 2/1997 |
| GB | 2261290 | 5/1993 |
| NL | 8802817 | 6/1990 |
| WO | 9425841 | 11/1994 |
| WO | 9507048 | 3/1995 |

* cited by examiner

Primary Examiner—Jeffery Hofsass
Assistant Examiner—Daniel Previl
(74) Attorney, Agent, or Firm—Edwin D. Schindler

(57) ABSTRACT

An alert device for providing a warning of a baby's condition which may lead to the onset of SIDS. The alert device includes a receiver for receiving a signal, which has an element for warning a person proximate to the receiver of the baby's condition. A transmitter for transmitting a signal to the receiver includes a device for connecting the transmitter to a baby and is located remotely from the receiver. A transducer includes a device for connecting the transducer to a baby's chest, with the transducer further including a pressure-sensitive and/or a temperature-sensitive activation element to be located on the baby's chest. The pressure-sensitive and/or temperature-sensitive activation element is activated when the baby rolls over onto the baby's chest, a position which has been associated with the onset of SIDS, so that the transducer causes signalling of the transmitter to, in turn, signal the receiver, for warning a person located proximate to the receiver and located remotely from the baby, when the receiver receives the signal, that the baby's condition may lead to the onset of SIDS.

20 Claims, 18 Drawing Sheets

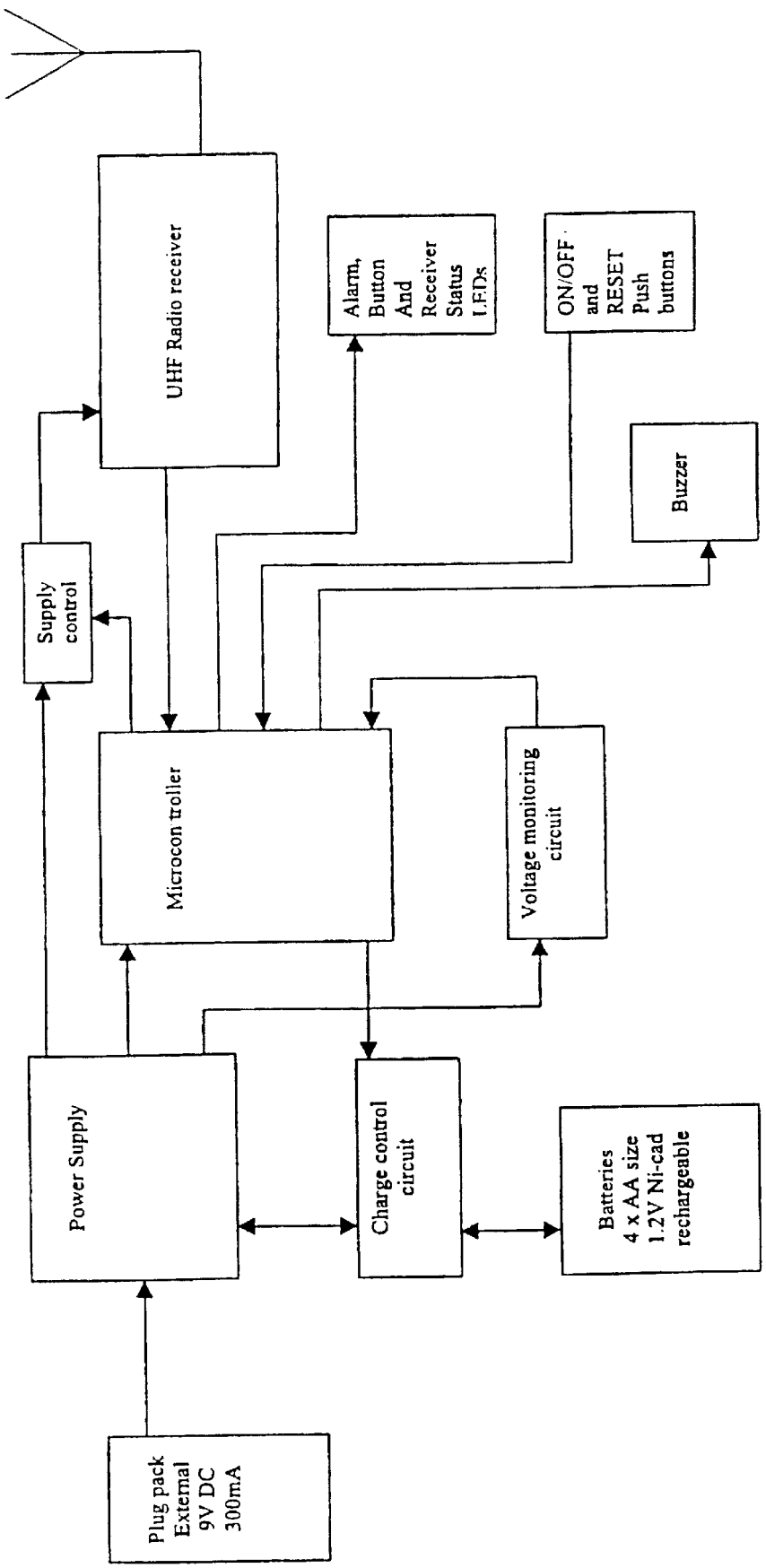

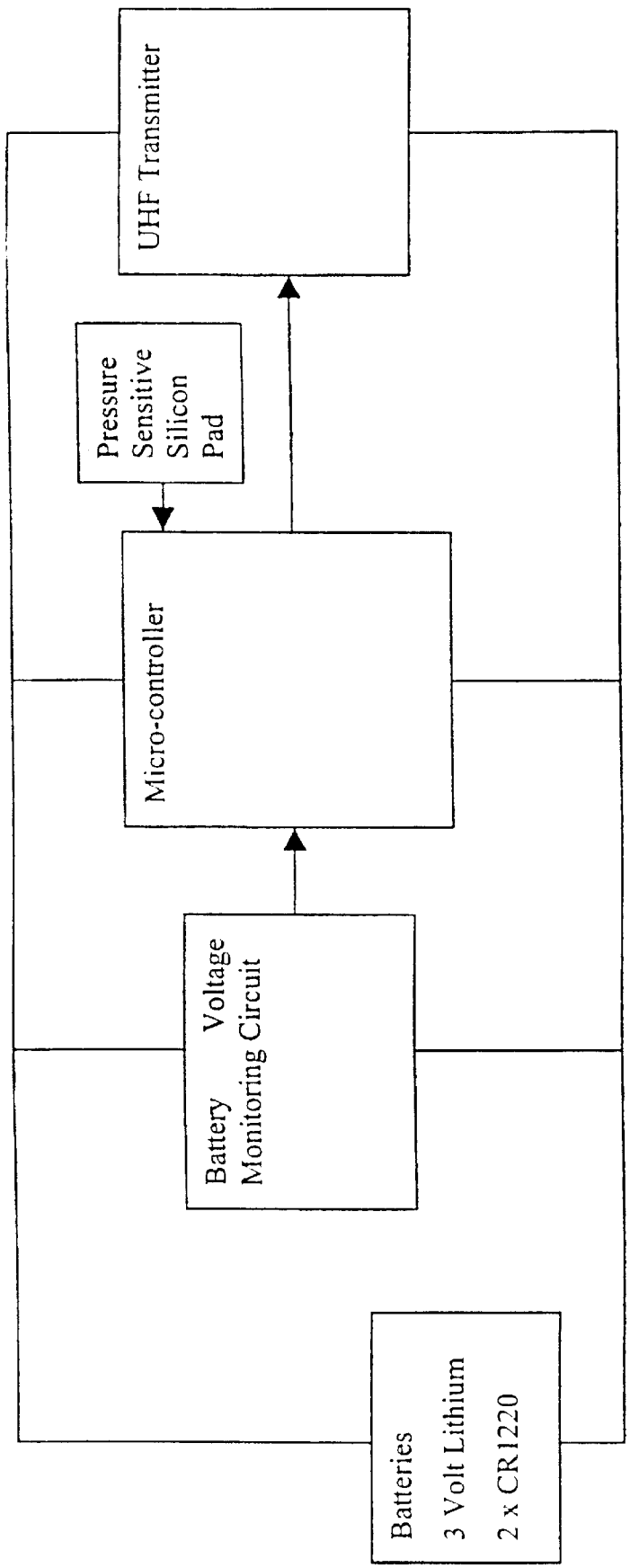
FIG_3

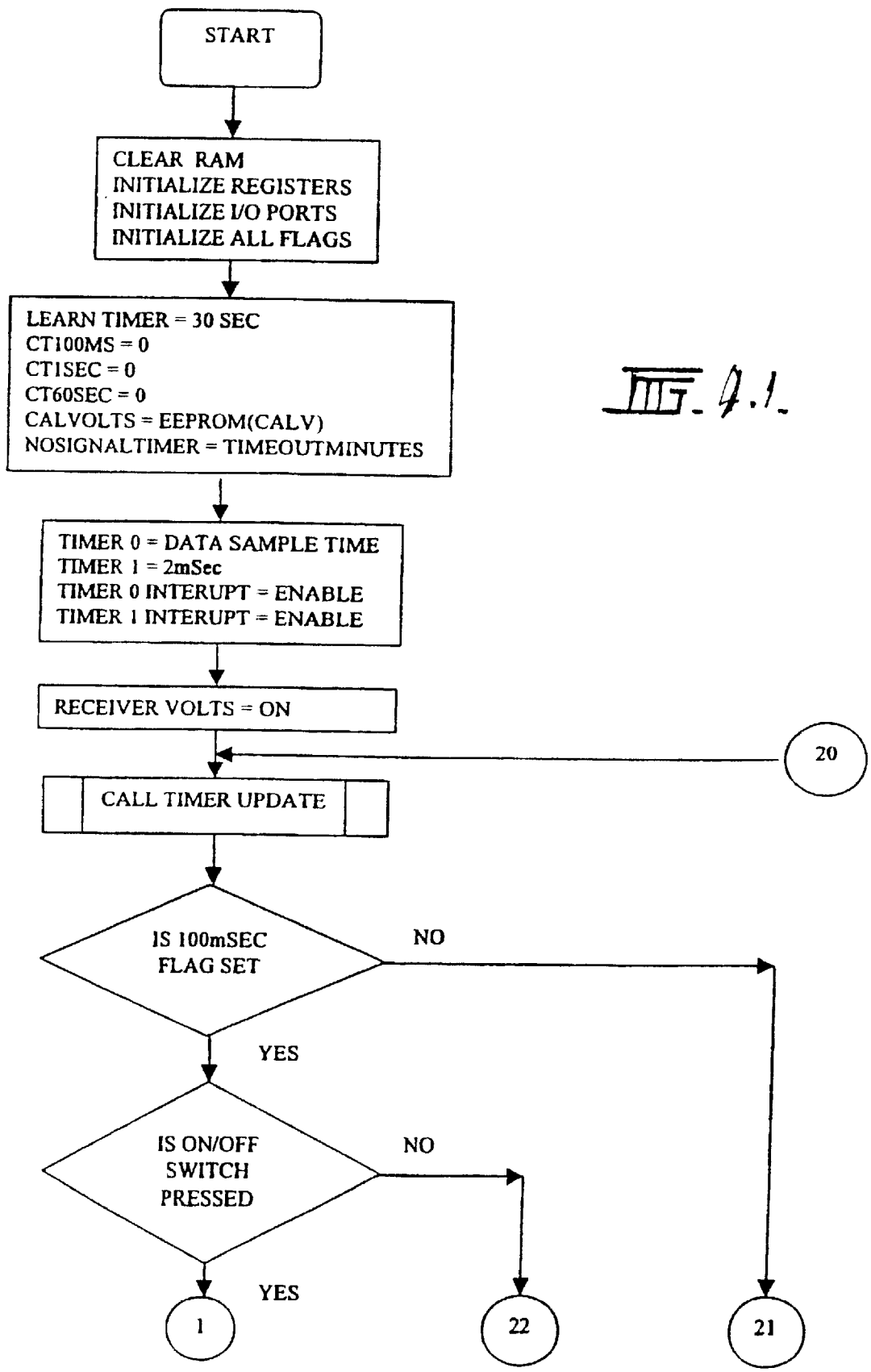
FIG. 4.1.

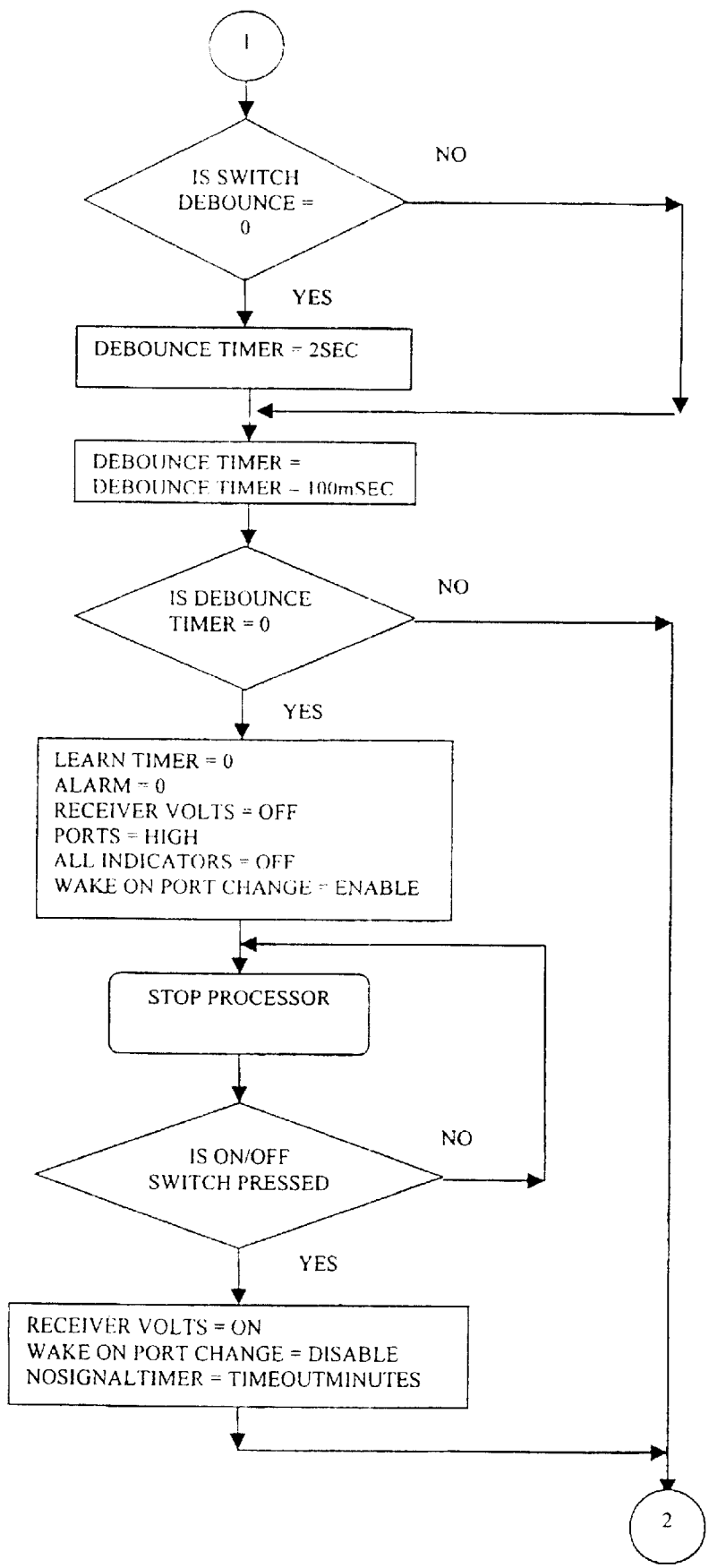
FIG. 4.2

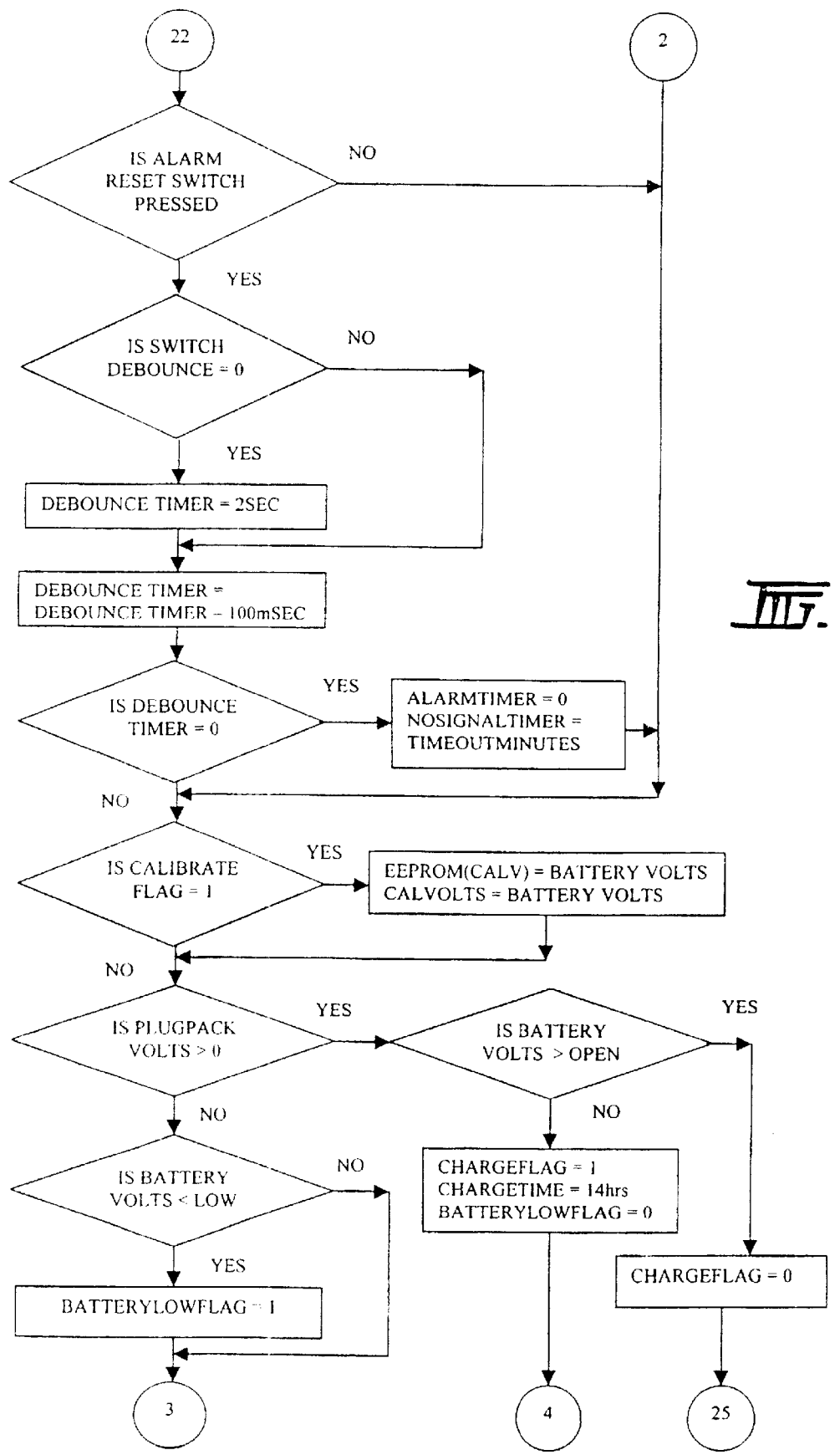
FIG. 4.3

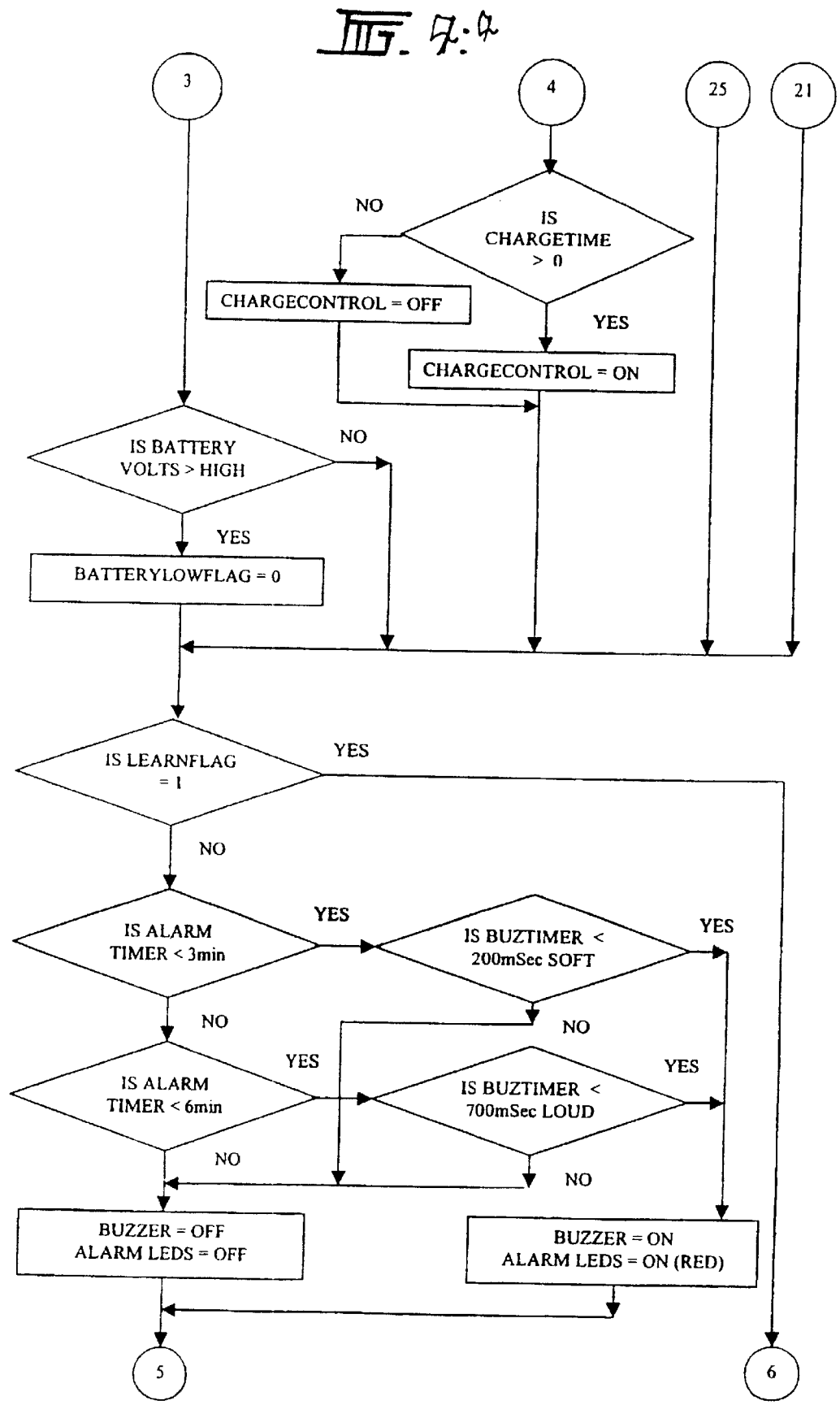

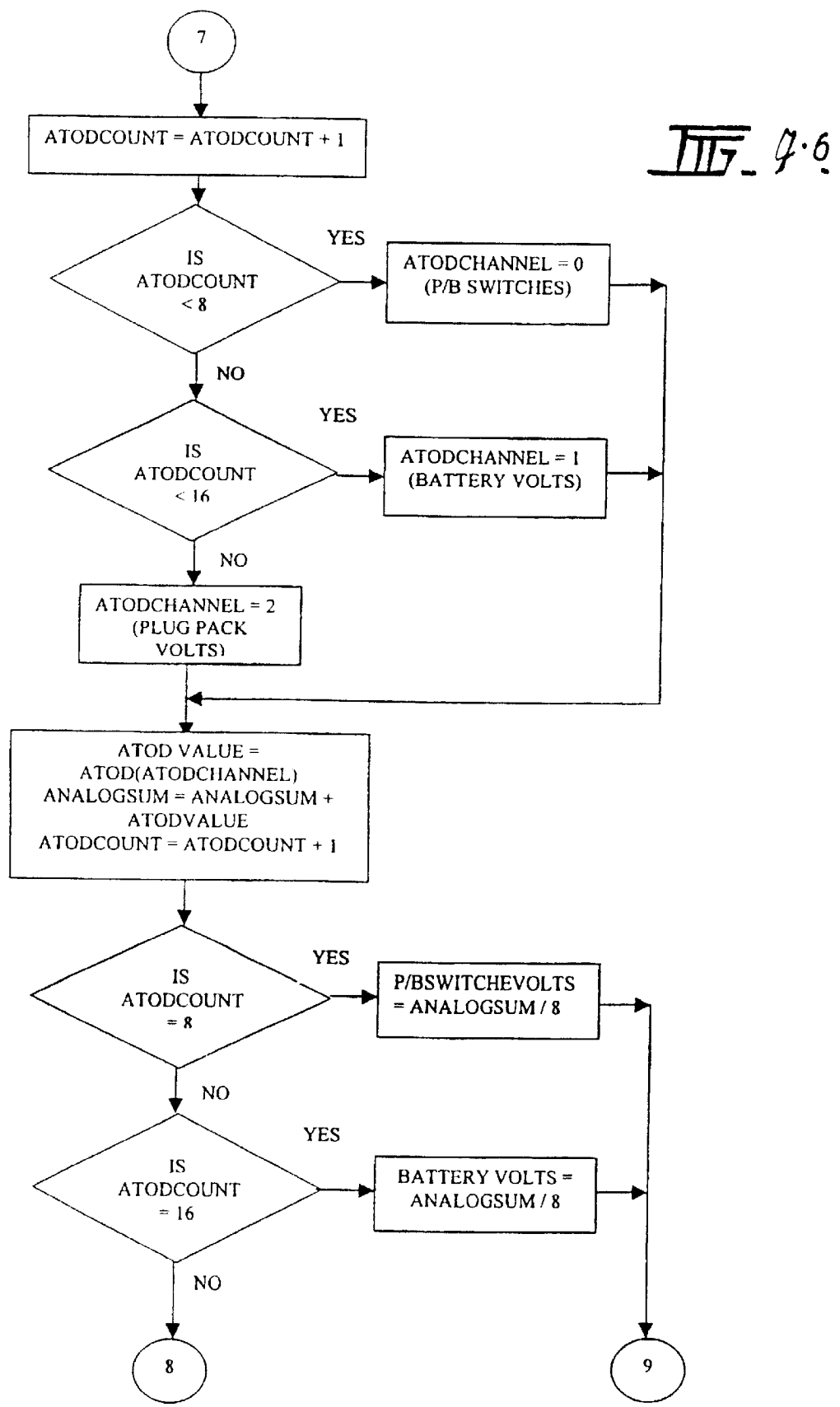
FIG. 9.6

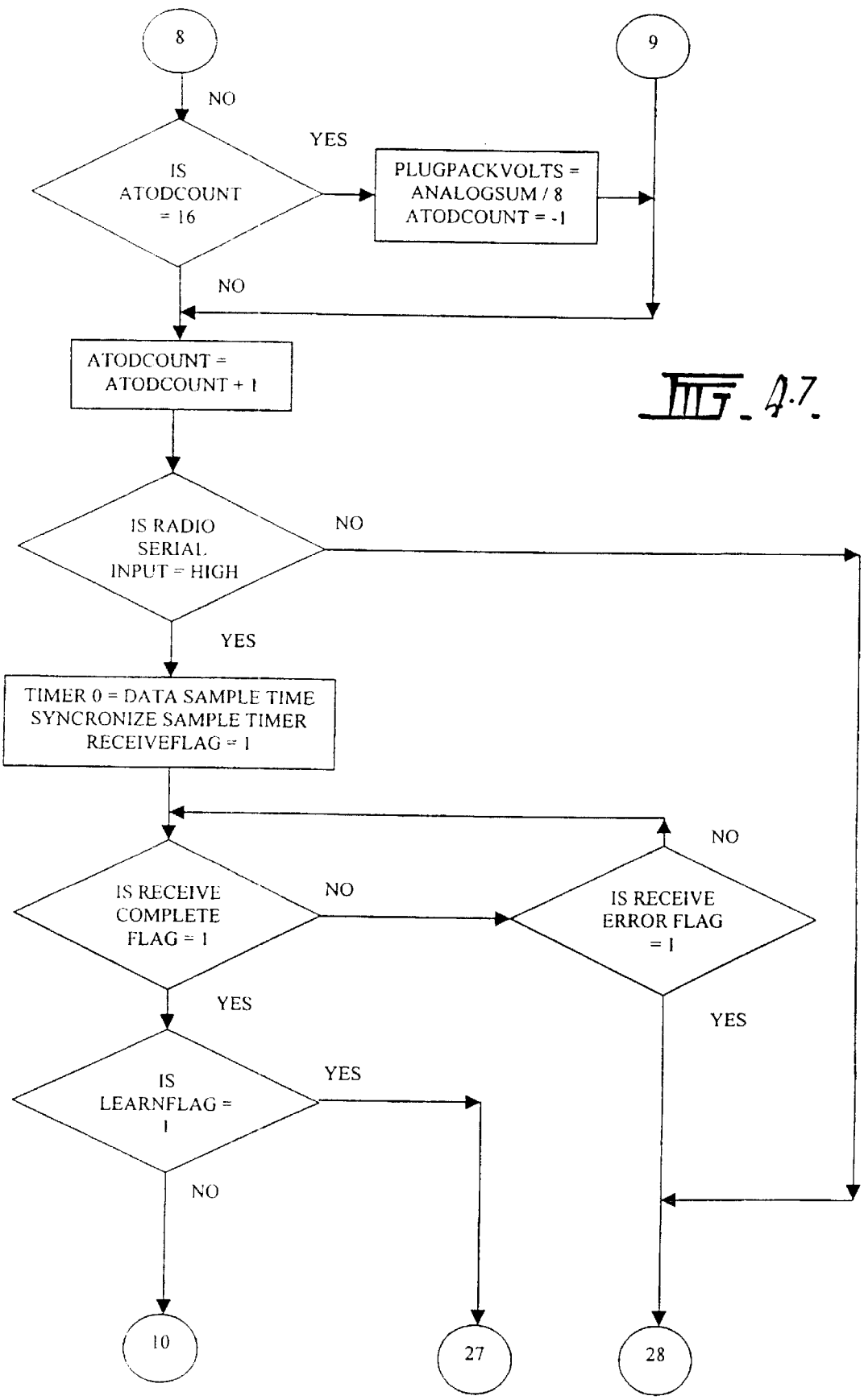
FIG. 4.7.

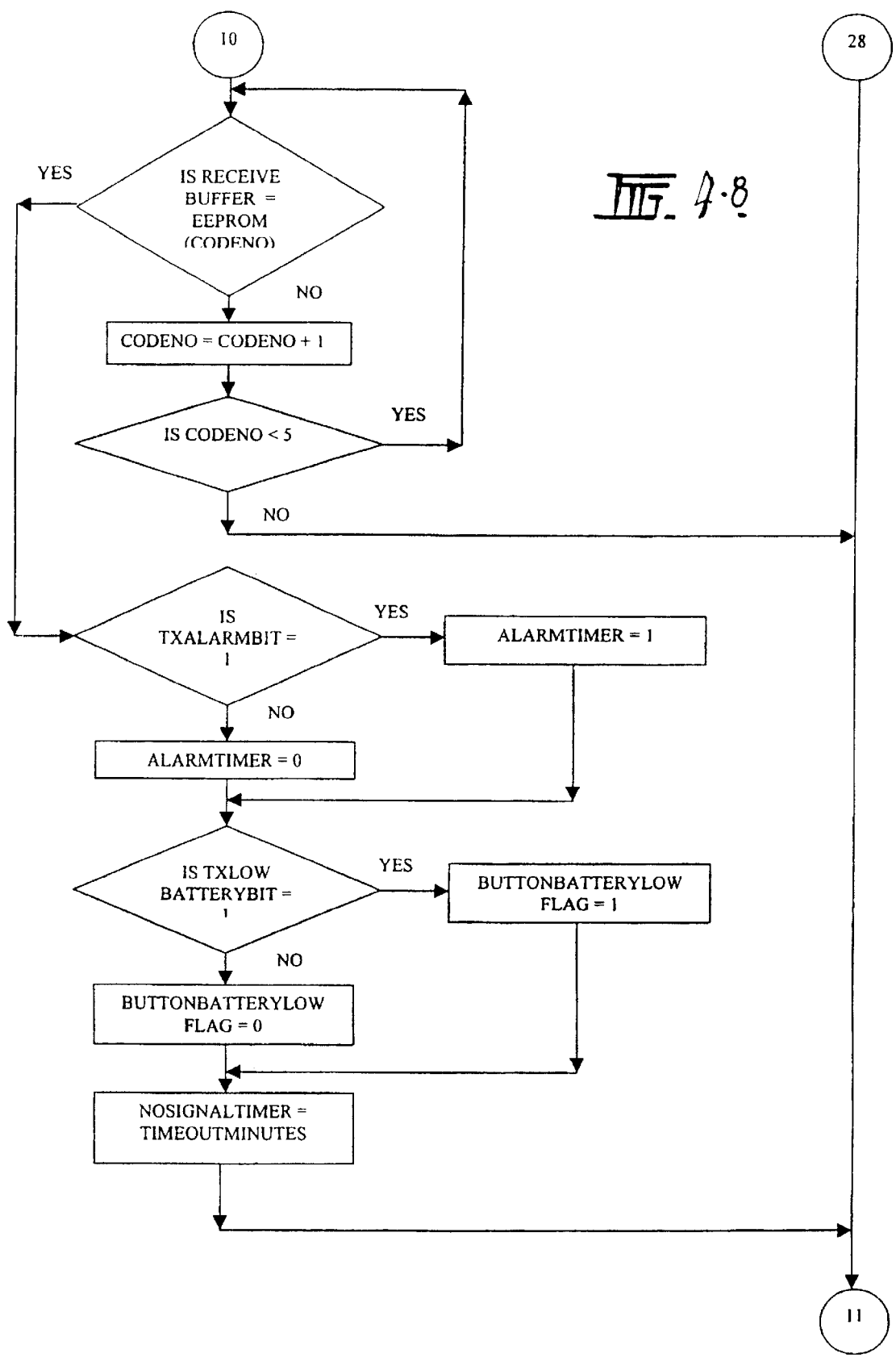

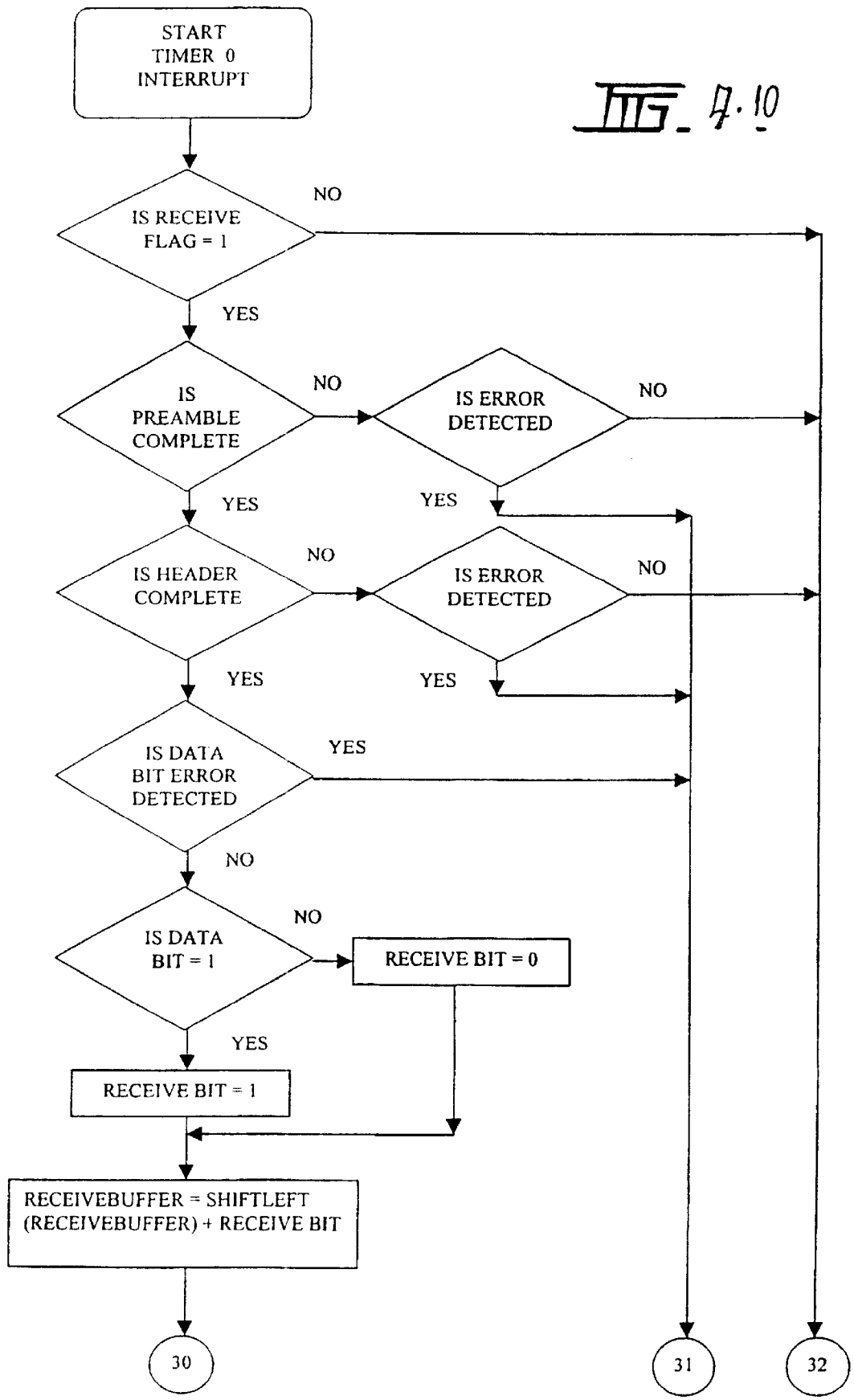
FIG. 4.10

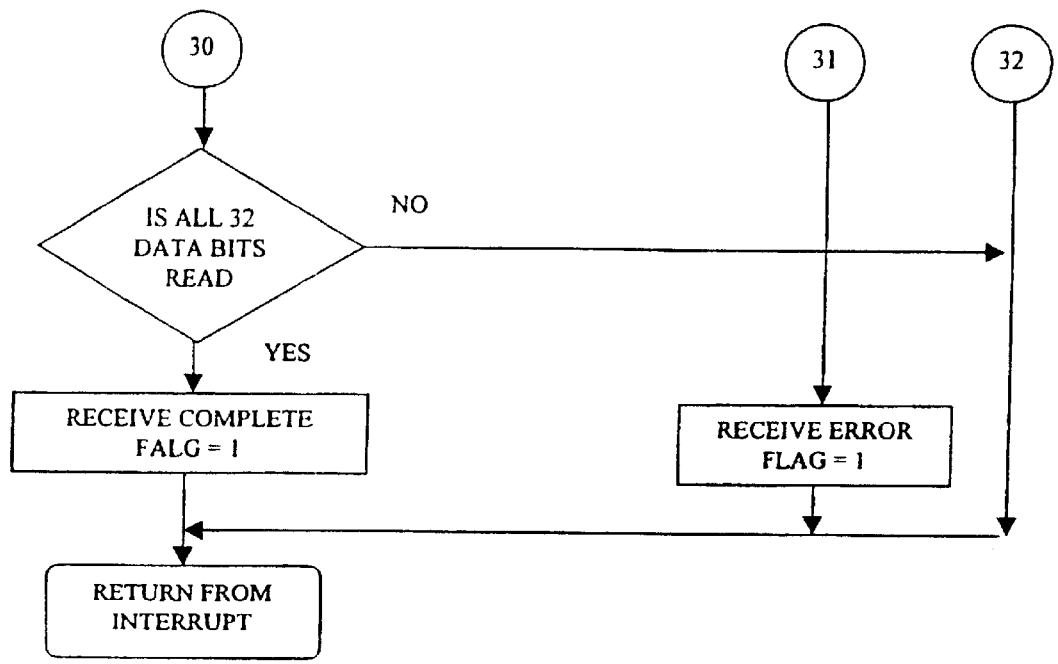
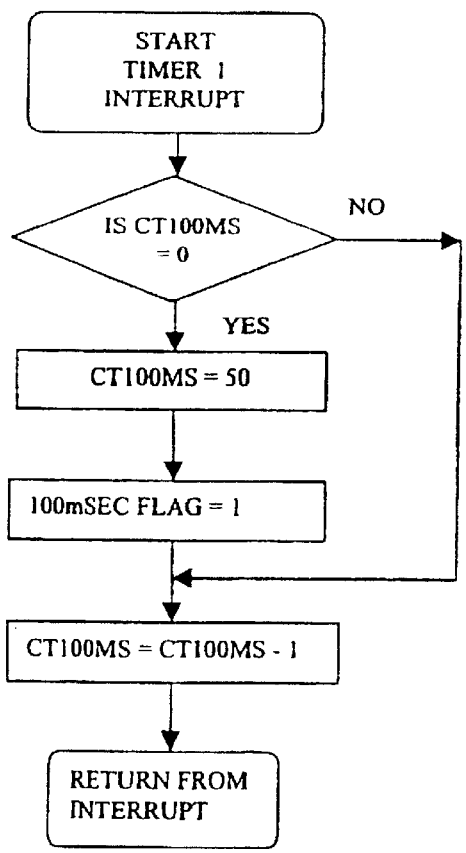
FIG. 7-11

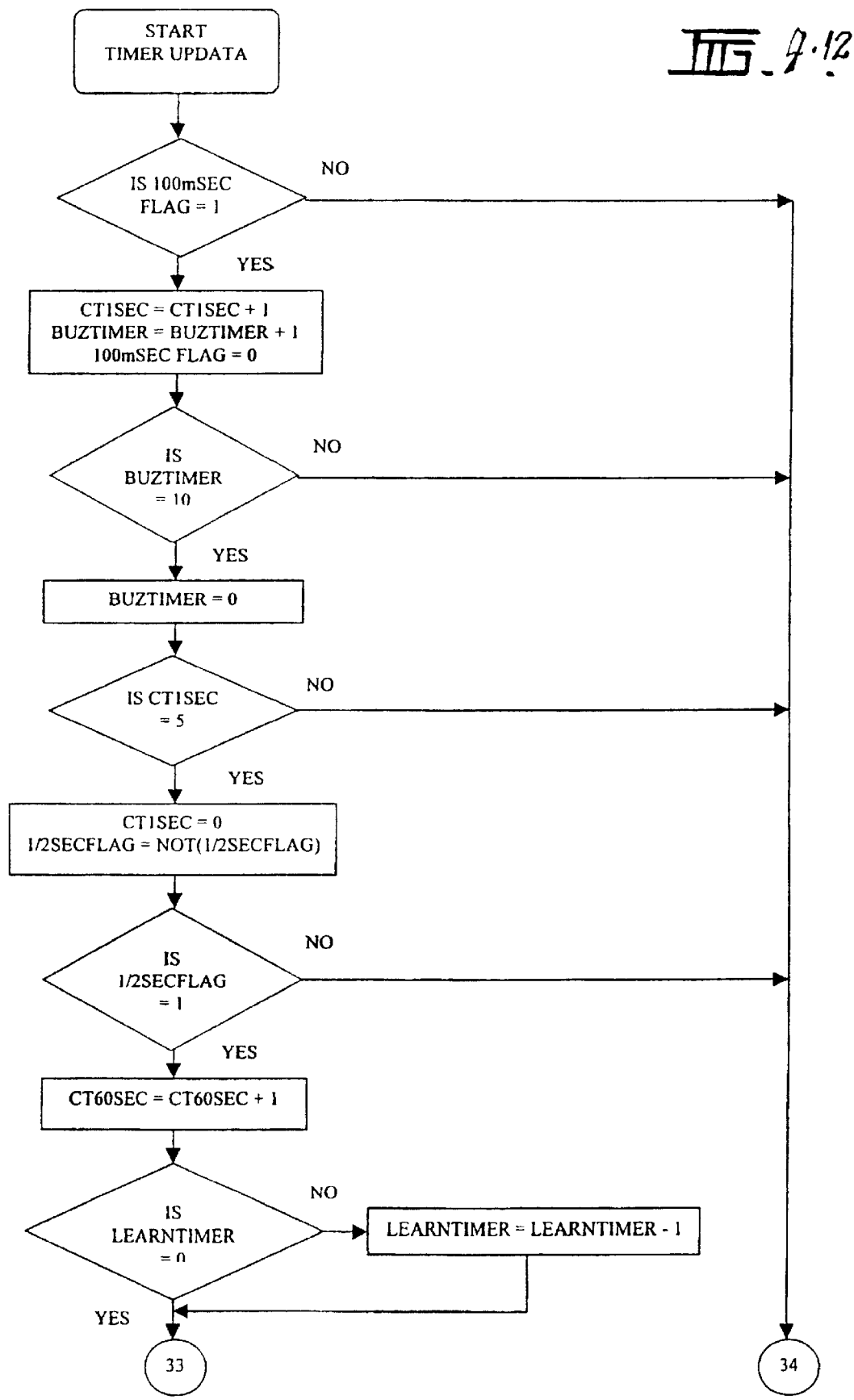

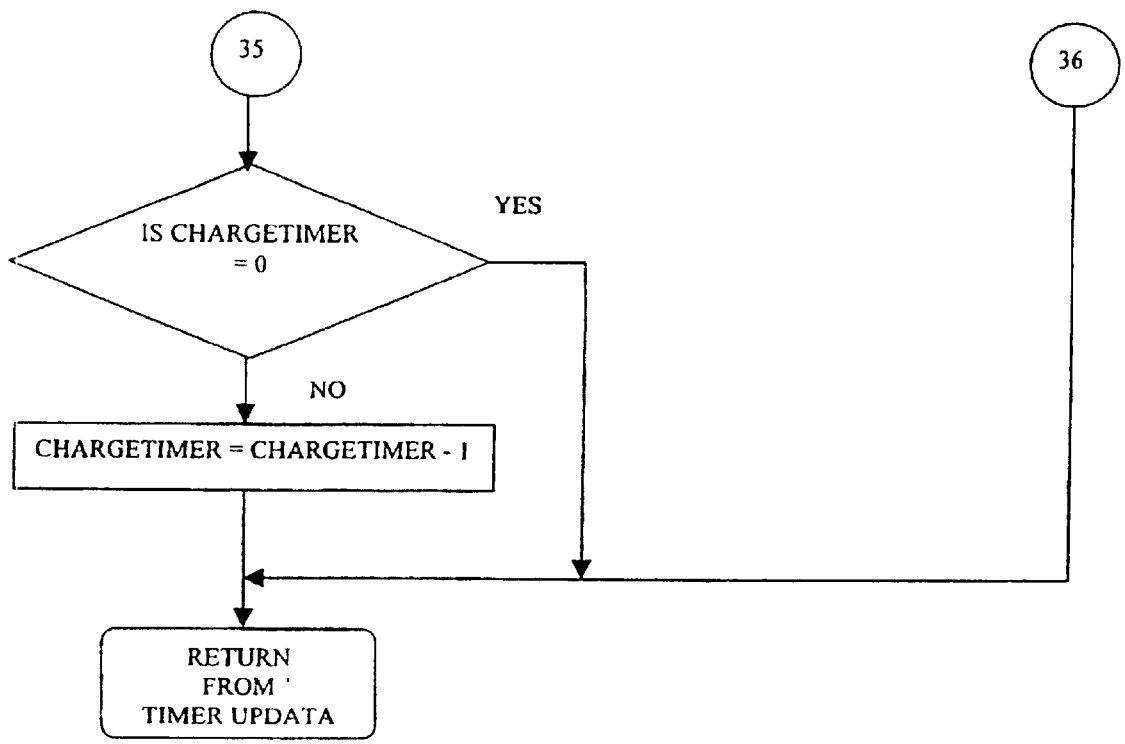
FIG. 19.14

ALERT DEVICE FOR PROVIDING A WARNING OF A BABY'S CONDITION WHICH MAY LEAD TO THE ONSET OF SIDS

BACKGROUND OF THE INVENTION

1. Technical Field of the Invention

This invention relates to an alert device and in particular for such a device to be used to indicate the position of a baby or child, so that parent or guardian at a remote position can be notified if the baby rolls over onto its stomach and/or to provide an indication if there is an undesirable change in the temperature of the baby.

2. Description of the Prior Art

Medical practitioners and researchers have found that the likelihood of a baby or child up to 24 months old (hereinafter for convenience a called a "baby"), suffering from Sudden Infant Death Syndrome (SIDS) or "Cot Death" is greatly increased if the baby sleeps on its stomach, so, generally, parents are told to have their baby sleep on his or her back.

Of course, many babies are restless during sleep, and on occasions will roll themselves over until they are lying on their stomach.

Also, unexpected changes in the temperature of the baby should lead to a check of the baby.

SUMMARY OF THE INVENTION

The object of the present invention is to provide means whereby when, either or both these events occur parents or guardians will receive an immediate notification, so that they can take steps to turn the baby over or to check the baby's temperature.

The invention, in its broadest sense, comprises an alert device having a transmitter device adapted to be connected to a baby or its clothes, which device has a transducer which is operated on a particular event occurring, and when the transducer is activated the transmitter is caused to send a signal to a receiver which can be at a remote position which signal activates an alarm response at the receiver.

The event can be on the baby rolling over and its weight being applied to the transducer or a change in temperature of the baby.

The device is also preferably provided with check means whereby the status of the transmitter is automatically monitored by the receiver.

BRIEF DESCRIPTION OF THE DRAWING FIGURES

In order that the invention may be more readily understood, we shall describe in relation to the accompanying drawings, embodiments of the alert device of the invention.

In these drawings:

FIG. 2 is a block diagram of the monitor receiver;

FIG. 3 is a block diagram of the baby button;

DETAILED DESCRIPTION OF THE DRAWING FIGURES AND PREFERRED EMBODIMENTS

Figure 1:
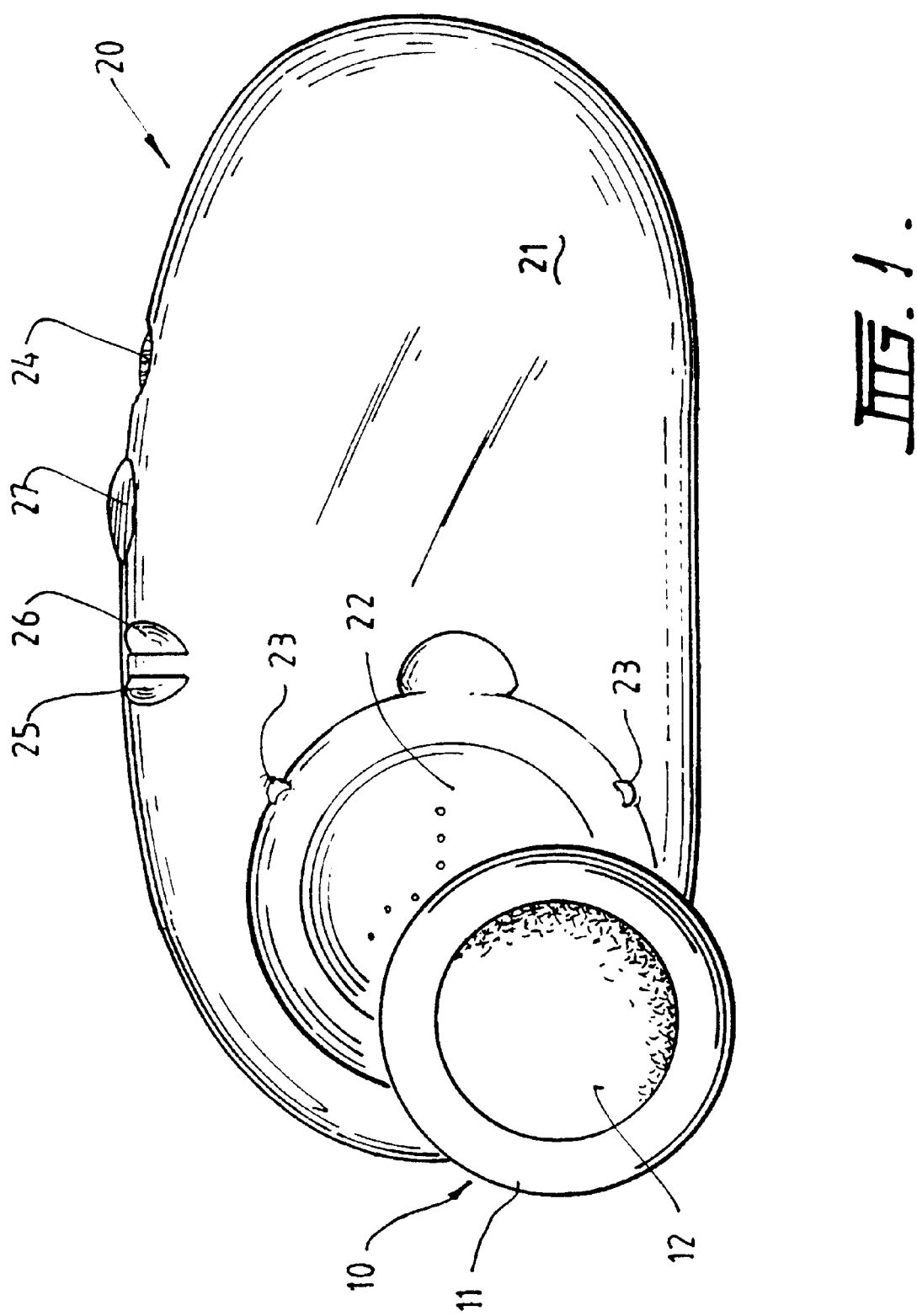
FIG. 1 shows the monitor and the "baby button" of a preferred form of device, the two components being shown slightly separated.

The device illustrated is to provide an indication as to when the baby rolls over.

The monitor device has two components, the baby button or transmitter 10, which is adapted to be fitted to the baby, and the receiver 20.

The baby button has a casing 11 being a plastics moulding, which is adapted to be connected to the baby's clothing, as by an integral clip in the underside thereof or may have means whereby safety pins or the like could be used to connect the baby button. The baby button is preferably waterproof, and has a member 12 extending from its face which may be of a flexible material or a moveable button which is connected to a transducer, which may be a pressure sensor which is activated by pressure on the member 12.

The member 12 is of a sufficient size as to be operated whenever the baby turns over notwithstanding the actual final position of the baby and the baby button itself is of such a size and shape as to be not uncomfortable for the baby.

The transmitter can be operated by an internal battery, preferably a lithium battery, and may be adapted to operated either 315 MHZ or 433.92 MHZ, that is in the frequency ranges permitted for the devices of this type in Australia, or any other acceptable frequency.

The receiver 20 also has a casing 21 which can be a plastics moulding and as a recess 22 which is adapted to receive the baby button 10 when this is not in use. The recess 22 can have lugs 23 to hold the baby button 10. The receiver is also operated by rechargeable batteries and the interconnection of the button and the receiver is such that a charging circuit causes both the components to be recharged at the one time.

At the rear of the casing, the receiver may be provided with a belt clip whereby when the device is in use a parent or carer (hereinafter, for convenience, referred to as a parent) can clip the receiver to his or her belt so that the receiver is maintained in close relationship to the parent.

The receiver has a power button whereby it can be switched to an operating condition when it is to be used and there may be a battery isolation switch in the battery compartment whereby if the unit is not to be used for some time, the battery(ies) can be disconnected from the electronic circuit.

It also has and indicator light 26 for the operation of the baby button and an indicator light 25 to indicate that the receiver is operating.

The indicator light 26 for the operation of the baby button can be arranged to flash green when the monitor is operating correctly and red if the battery is low. The indicator light for the receiver may be unilluminated when the receiver is operating correctly and flash red when the battery(ies) need recharging. It may be arranged to be green when the battery is connected to a charger.

The receiver also has a warning light and reset 27 which, when the alarm is activated provides a visible and audible warning for the parent. The reset can be operated after the parent has gone to the baby and replaced it into a position where the baby button is not activated.

In use, the power button 24 on the receiver is actuated there is an audible "Beep" and the indicator lights 25,26 blink. This is a battery save position and also the set up used when the battery is to be charged. If the button 24 is then held down, there will be a longer beep, the indicator lights flash and the baby button indicator remains illuminated, this being an indication that the device is working correctly.

Under normal operating conditions the transmitter 10 is not activated but it does monitor its own battery level.

At regular intervals, say once every 60 minutes, the transmitter 10 will send a signal to the receiver/monitor 20 to confirm its correct operation. This signal will, as well as purely relating to the proper operation of the transmitter, include a component relating to a satisfactory voltage level of the battery.

If the battery voltage drops below a pre-determined level the baby button monitor light on the receiver will flash red to indicate the necessity of replacing or recharging the battery.

The signal will reset a timer in the receiver and if a further signal is not received in a further 60 minutes, then there can be an alarm signal which can cause the user to examine the transmitter. This alarm signal can be a low level alarm, as it is not in itself an indication the baby has rolled over.

When the baby wearing the device rolls over on to its chest, the body weight will cause pressure on the member 12 and cause actuation of the transducer. This will cause the button's transmitter to send an immediate status-alert signal to the receiver 20. If required this signal can also include material relating to the condition of the battery of the baby button.

If there is no acknowledgement of the alarm within a predetermined period, say three minutes, then the intensity of the audible alarm can be increased.

If after a further period, there has been no response, then the alarm can be shut down for a period, say one minute, and at the end of this time the cycle recommence.

The alert signal will continue to be sent and, if required can become faster and louder as time passes to indicate a situation which has the potential of being more concerning as time passes. Also, even if the baby again rolls from its non-acceptable position, the alarm can continue until there has been a physical check of the baby.

When the parent goes to the baby and it is rolled over from the position where the transducer was being actuated, the transducer is de-activated and the transmitter returns to its normal condition. The parent can by actuating the alarm button 27 reset this to cause the alarm signals to cease.

While we have described the use of rechargeable batteries in both the baby button and the receiver, these, or either of them, particularly the button, could use replaceable batteries.

Figures 4, 5:
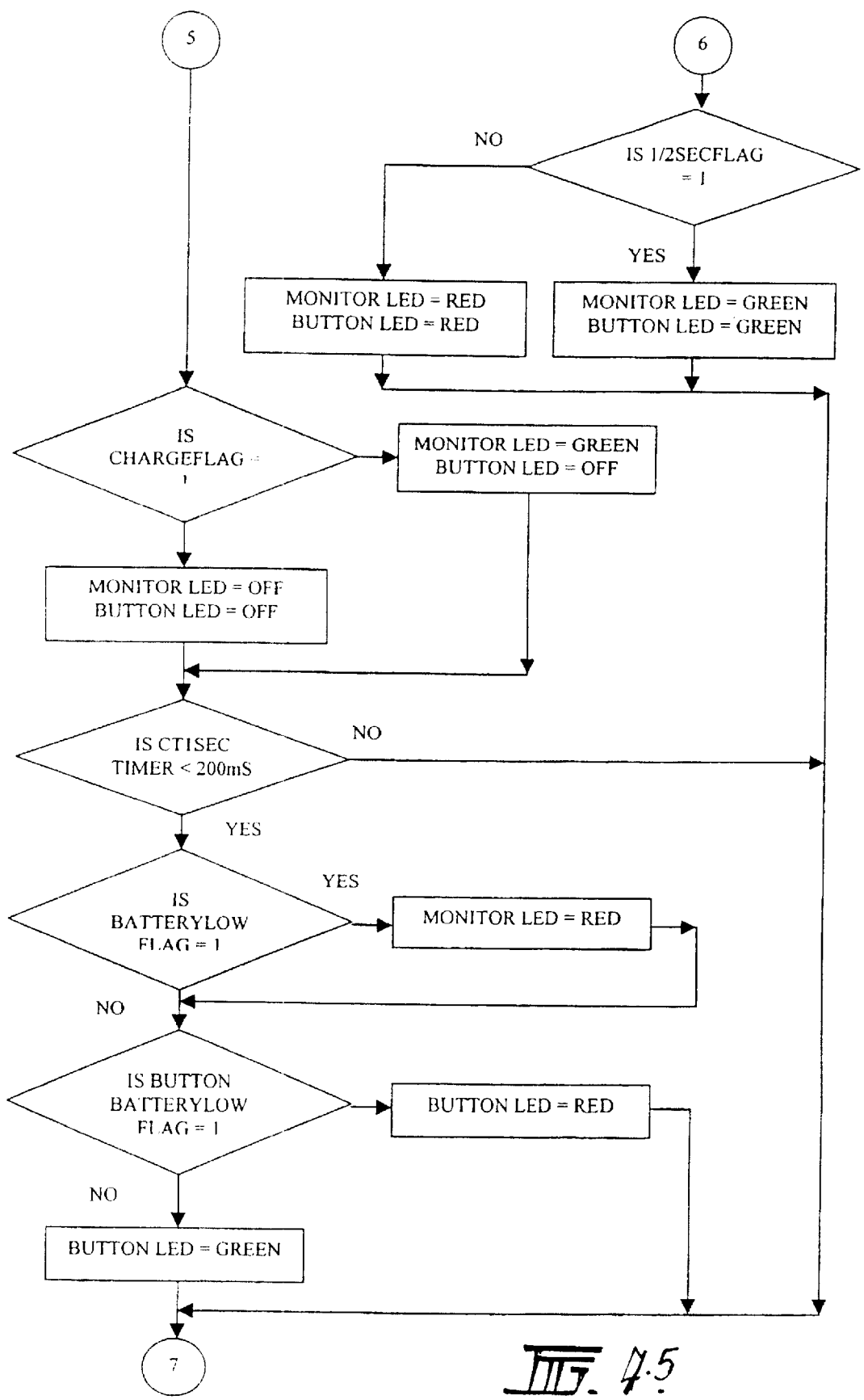
FIG. 4 (which comprises 14 sheets) is a flow chart of the monitor receiver.
FIG. 5 is a flow chart of the baby button.
Figures 4, 5, 6, 7, 8, 9:
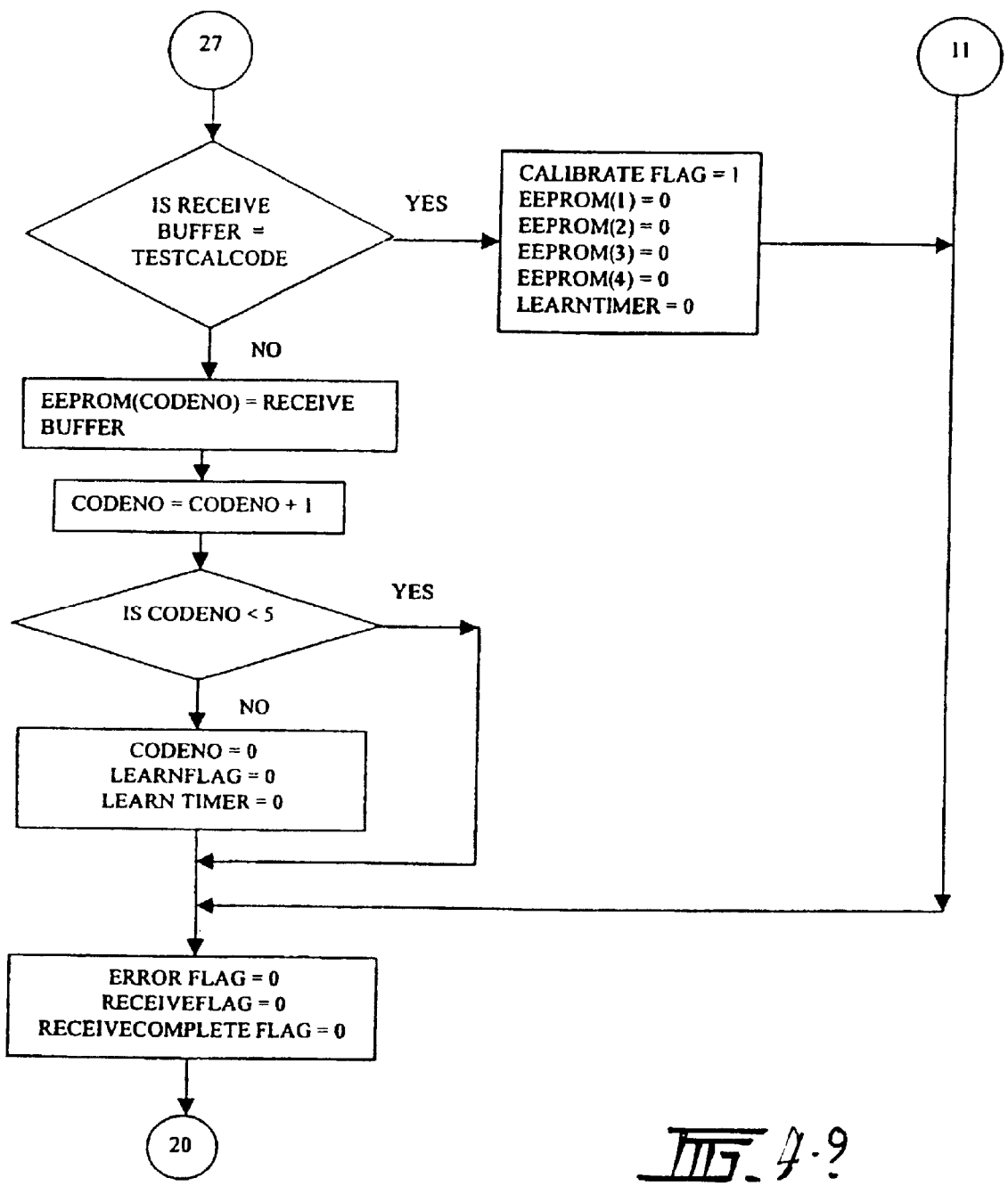
Figures 9, 10, 11, 12, 13:
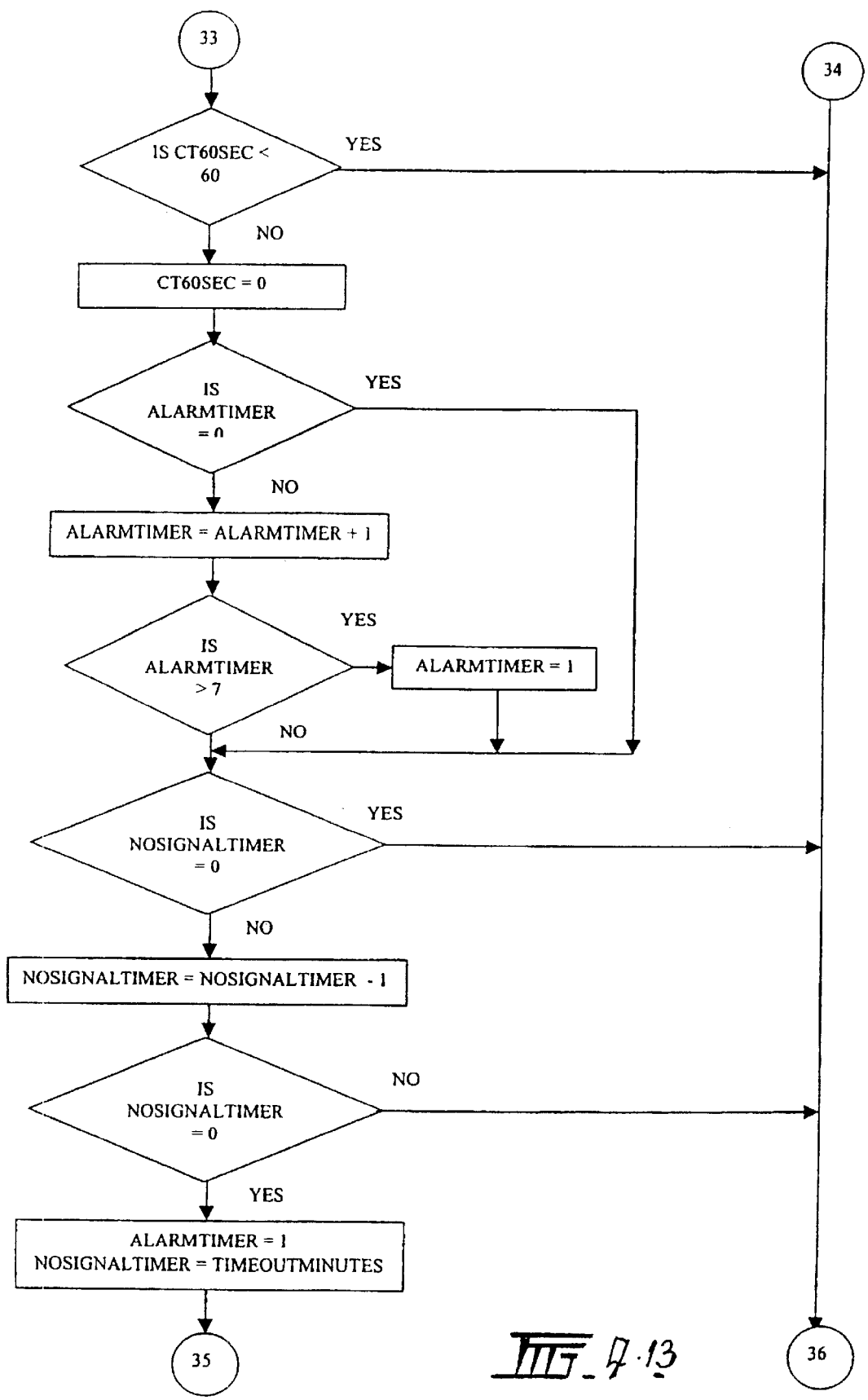
Figure 5:
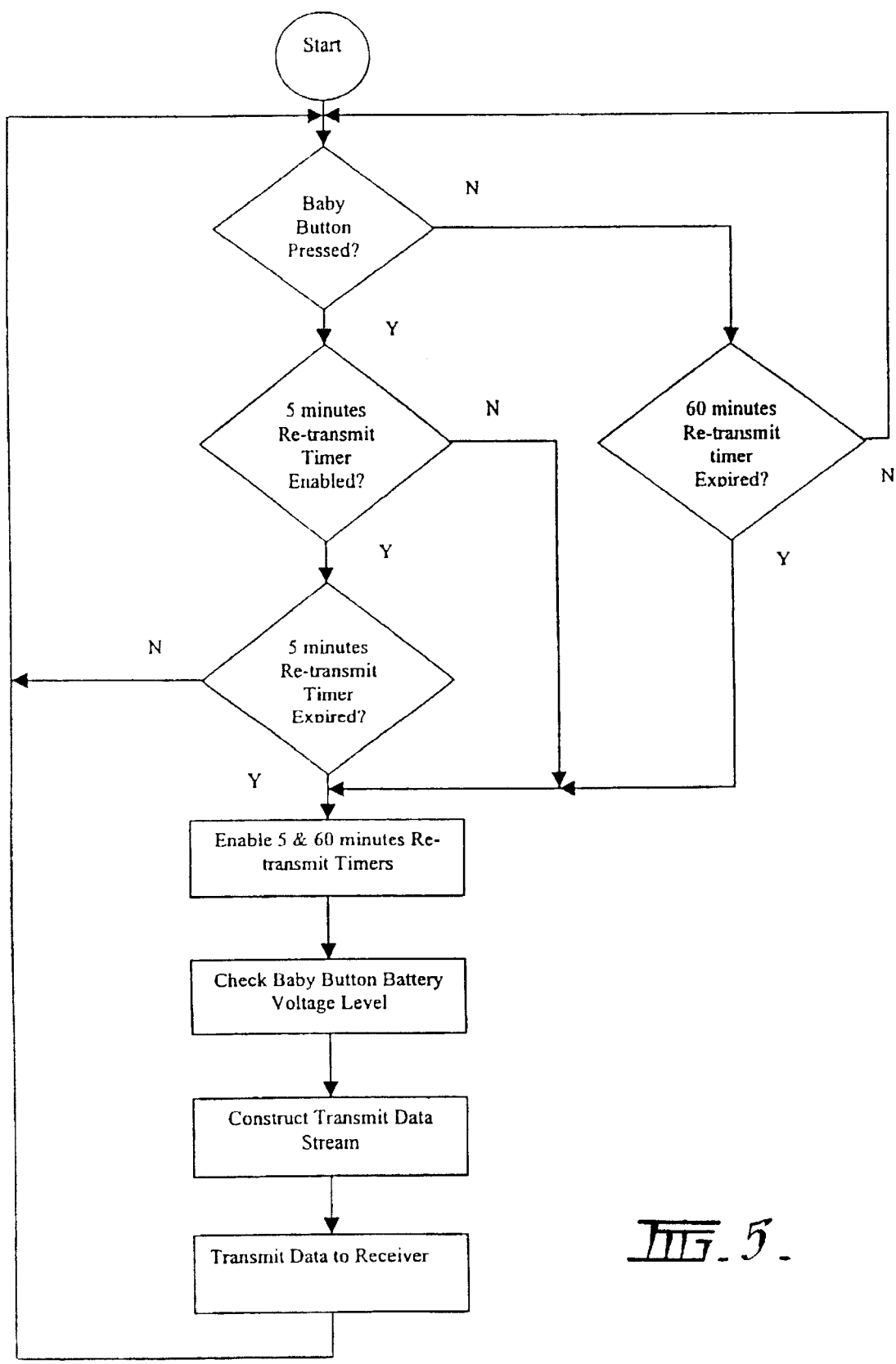

FIGS. 2 to 5 show schematic block diagrams of the baby button and the receiver and the logical flow chart for each of these. In the light of the discussion above, these figures are self explanatory to one skilled in the art and will not be further discussed.

The power and the operating frequency of the transmitter, must be in a range which is acceptable in the country in which the device is to be used. The power could be such as to provide reception over about 50 meters and the frequency could be, as mentioned, in Australia be 315 MHZ or 433.92 MHZ In a second embodiment of the device, which could be used alone but normally would be used in association with the first embodiment, changes in the baby's temperature or a change in absolute temperature is monitored.

In this case the transducer may preferably be in contact with the baby's skin, and could be located on the chest and held in position by straps having connectors of Velcro (registered trade mark) ends which do not unduly inhibit the baby's movements and are not uncomfortable if lain upon.

In this case the temperature transducer would be on the side of the device closest to the baby's body, and the pressure transducer could as described in the earlier embodiment extend from the other side, or there could simply be a transducer in the device which is operated by pressure.

The actual operation of this device could be considered to be very similar to that previously described, and will not be described further except to say that the alarm condition is established when there is either a change in the baby's temperature at a rate faster than a predetermined change, or the baby's temperature reaches or drops to a predetermined temperature.

In each case the audible and visible alarm will be initiated so that, as in the previous embodiment, the situation of the baby can be checked by the parent.

As in some households/institutions, there may be a number of babies, it is preferred that the monitor could be used to monitor a number of the transmitter devices. The system can be provided with a Learn Mode, which can be actuated by an operator, and while in this mode the transmitters of each of the units to be monitored can be physically operated to send an alarm signal and the receiver can identify each of these signals, and, on monitoring, should any one of the alarm devices be actuated or have another fault condition, then this can be ascertained.

It is possible under the circumstances, that the light associated with the Alarm/Acknowledge button, could be caused to flash with different signals for the different transmitters.

That is, during the Learn Mode each transmitter could be associated with a particular signal. If, say, the device is adapted to monitor four transmitters, then the transmitters could be associated with a number of flashes depending upon the order in which they are entered on the Learn Function.

I claim:

1. An alert device for providing a warning of a baby's condition which may lead to the onset of SIDS, comprising:
    a receiver for receiving a signal, said receiver including means for warning a person proximate to said receiver;
    a transmitter having means for connecting said transmitter to a baby and being located remotely from said receiver, said transmitter incorporating means for signalling said receiver; and,
    a transducer having means for connecting said transducer to a baby's chest with said transducer further including pressure-sensitive activation means to be located on the baby's chest, said pressure-sensitive activation means being activated when the baby rolls over onto the baby's chest, so that said transducer causes said means for signalling of said transmitter to signal said receiver, thereby warning a person located proximate to said receiver and located remotely from the baby, when said receiver receives the signal, that the baby's condition may lead to the onset of SIDS.

2. The alert device according to claim 1, wherein said transducer further includes temperature-sensitive activation means activated upon a change in temperature of the baby at a rate exceeding a predetermined rate of change for the temperature of the baby, said temperature-sensitive activation means activating said transducer, so that said transducer causes said means for signalling of said transmitter to signal said receiver.

3. The alert device according to claim 1, wherein said transmitter further includes means for transmitting an indication that said transmitter is operating properly, said means for transmitting an indication being activated at a predetermined interval of time.

4. The alert device according to claim 1, wherein said transmitter further includes means for transmitting an indication of battery voltage for said transmitter when the battery voltage falls to a predetermined level.

5. The alert device according to claim 1, wherein said means for warning of said receiver, upon receiving a signal from said transmitter, provides an audible signal to a person proximate to said receiver.

6. The alert device according to claim 1, wherein said means for warning of said receiver, upon receiving a signal from said transmitter, provides a visual signal to a person proximate to said receiver.

7. The alert device according to claim 6, wherein said means for warning of said receiver includes means for acknowledging a warning.

8. The alert device according to claim 7, wherein said means for acknowledging a warning includes means for rendering the warning more insistent if said means for acknowledging is not activated within a predetermined period of time.

9. The alert device according to claim 1, further comprising a plurality of said transmitters for signalling said receiver, with said receiver having means for discriminating signals from each of said plurality of said transmitters.

10. The alert device according to claim 1, wherein said receiver is a button connected to clothing worn by the baby.

11. An alert device for providing a warning of a baby's condition which may lead to the onset of SIDS, comprising:

a receiver for receiving a signal, said receiver including means for warning a person proximate to said receiver;

a transmitter having means for connecting said transmitter to a baby and being located remotely from said receiver, said transmitter incorporating means for signalling said receiver; and, a transducer having means for connecting said transducer to a baby's chest with said transducer further including temperature-sensitive activation means to be located on the baby's chest, said temperature-sensitive activation means being activated upon a change in temperature of the baby, said temperature-sensitive activation means activating said transducer when the baby rolls over onto the baby's chest, so that said transducer causes said means for signalling of said transmitter to signal said receiver, thereby warning a person located proximate to said receiver and located remotely from the baby, when said receiver receives the signal, that the baby's condition may lead to the onset of SIDS.

12. The alert device according to claim 11, wherein said temperature-sensitive activation means of said transducer is activated upon a change in temperature of the baby at a rate exceeding a predetermined rate of change for the temperature of the baby, said temperature-sensitive activation means activating said transducer, so that said transducer causes said means for signalling of said transmitter to signal said receiver.

13. The alert device according to claim 11, wherein said transmitter further includes means for transmitting an indication that said transmitter is operating properly, said means for transmitting an indication being activated at a predetermined interval of time.

14. The alert device according to claim 11, wherein said transmitter further includes means for transmitting an indication of battery voltage for said transmitter when the battery voltage falls to a predetermined level.

15. The alert device according to claim 11, wherein said means for warning of said receiver, upon receiving a signal from said transmitter, provides an audible signal to a person proximate to said receiver.

16. The alert device according to claim 11, wherein said means for warning of said receiver, upon receiving a signal from said transmitter, provides a visual signal to a person proximate to said receiver.

17. The alert device according to claim 16, wherein said means for warning of said receiver includes means for acknowledging a warning.

18. The alert device according to claim 17, wherein said means for acknowledging a warning includes means for rendering the warning more insistent if said means for acknowledging is not activated within a predetermined period of time.

19. The alert device according to claim 11, further comprising a plurality of said transmitters for signalling said receiver, with said receiver having means for discriminating signals from each of said plurality of said transmitters.

20. The alert device according to claim 11, wherein said receiver is a button connected to clothing worn by the baby.

\* \* \* \* \*